(12) United States Patent
Ashimoto

(10) Patent No.: US 6,667,799 B2
(45) Date of Patent: Dec. 23, 2003

(54) METHOD AND APPARATUS FOR INSPECTING AN EXTRUDED TREAD

(75) Inventor: Noriyoshi Ashimoto, Tokyo (JP)

(73) Assignee: Kabushiki Kaisha Bridgestone, Tokyo (JP)

( * ) Notice: Subject to any disclaimer, the term of this patent is extended or adjusted under 35 U.S.C. 154(b) by 0 days.

(21) Appl. No.: 10/231,049

(22) Filed: Aug. 30, 2002

(65) Prior Publication Data

US 2003/0067597 A1 Apr. 10, 2003

(30) Foreign Application Priority Data

Sep. 3, 2001 (JP) .................................. 2001-266218

(51) Int. Cl.⁷ ............................................. G01N 21/00
(52) U.S. Cl. ............................... 356/237.1; 356/237.2
(58) Field of Search ............................ 356/237.1, 237.2, 356/429–430; 73/146, 7, 8, 9

(56) References Cited

U.S. PATENT DOCUMENTS 3,596,274 A * 7/1971 Heringhaus ............ 250/559.45
3,918,816 A * 11/1975 Foster et al. ................ 356/602
5,801,304 A *  9/1998 Cantu et al. .................. 73/146
6,151,959 A * 11/2000 Cantu et al. .................. 73/146

FOREIGN PATENT DOCUMENTS

JP          6-18233       *  1/1994

* cited by examiner

Primary Examiner—Michael P. Stafira
(74) Attorney, Agent, or Firm—Sughrue Mion, PLLC

(57) ABSTRACT

A method and apparatus capable of inspecting the internal structure of an extruded tread efficiently and accurately on an on-line basis.

Image data on the cut section of the extruded tread photographed by a CCD camera is processed by a tread internal structure inspection unit to calculate the brightnesses of rubber layers which differ in composition, the boundaries among the rubber layers on the cut section are located from differences among the calculated brightnesses of the rubber layers, and it is judged whether the internal structure of the photographed extruded tread is satisfactory or not by comparing the above boundaries with preset reference boundaries.

3 Claims, 2 Drawing Sheets

METHOD AND APPARATUS FOR INSPECTING AN EXTRUDED TREAD

BACKGROUND OF THE INVENTION

1. Field of the Invention

The present invention relates to a method and apparatus for inspecting an extruded tread and, particularly, to a method and apparatus for checking the internal structure of an extruded tread on an on-line basis.

2. Description of the Prior Art

FIG. 4 is a diagram showing the outline of a tread extrusion step in which a rubber material produced in an unshown rubber kneading step is shaped like a belt by a warmer 51, supplied to an extrusion molding machine 52 to be molded to have a predetermined cross section, cooled in a cooling water tank 53 and cut to a length corresponding to one tire by a cutting machine 54 such as a tread skiver. The above cut extruded tread 20 is placed on a belt conveyor 55 as conveying means, carried on a tread carrier to a molding step and laminated with another member such as a cord, bead or belt on the molding machine to be assembled into one crude tire. In the figure, a molding machine for molding a single rubber material is illustrated to make the figure simple. A multilayer extruder for extruding different kinds of rubber at the same time is widely used as the extrusion molding machine. To cut the rubber material, the belt-like tread may be wound up by a winder and then cut when it is wound a required length.

After cutting, the outer shape, length, width and the like of the above extruded tread 20 and further the mass thereof are measured to check its quality for screening. These measurements are generally carried out on all the treads on an on-line basis.

The above extruded tread 20 consists of a plurality of rubber layers which differ from one another in composition. A material having excellent durability and abrasion resistance is used in a cap tread portion which is in contact with a road and a material having excellent adhesion to a cord, a small difference in stiffness from that of the cord and high hardness is used in a base tread portion which is in contact with the cord on the inner side. For the inspection of the tread, the cross section of the tread is observed and whether the internal structure of the extruded tread 20, that is, the lamination state of the rubber layers is good is judged from differences in gloss among rubber layers caused by use of different materials in the laminated rubber layers.

However, the above inspection is carried out by cutting a trial sample manufactured for an extrusion test prior to the actual production or a sample extracted from a production lot of actually extruded products and measuring the sample with the eye or loupe on an on-line base. Therefore, the production line cannot be re-started until the inspection result of the above internal structure is obtained, thereby reducing production efficiency.

To judge the internal structure by visual inspection accurately and quickly, an operator needs some skill. Therefore, it has been desired to simplify and increase the efficiency of the above inspection.

It is an object of the present invention which has been made in view of the problems of the prior art to provide a method and apparatus capable of checking the internal structure of an extruded tread efficiently and accurately.

SUMMARY OF THE INVENTION

According to a first aspect of the present invention, there is provided a method of inspecting an extruded tread, comprising the steps of:

photographing the cut section of an extruded tread;

processing the obtained image; and locating the boundaries among rubber layers on the above cut section from differences in brightness among the rubber layers which differ in composition.

This makes it possible to easily and accurately identify the boundaries among the rubber layers and to inspect the internal structure of the extruded tread without extracting an inspection sample from the production lot, whereby the inspection can be simplified and the efficiency of the inspection can be improved.

According to a second aspect of the present invention, there is provided an apparatus for inspecting an extruded tread, comprising:

means of photographing the cut section of an extruded tread, the means being installed near a line for conveying the extruded tread after cutting;

means of processing an image of the photographed cut section of the extruded tread to locate the boundaries among rubber layers which differ in composition on the cut section from differences in brightness among the rubber layers of the image; and means of judging whether the internal structure of the extruded tread is satisfactory or not by comparing the above located boundaries with preset reference boundaries.

Thus, the apparatus can check the internal structure of the extruded tread without extracting an inspection sample from the production lot.

According to a third aspect of the present invention, there is provided an apparatus for inspecting an extruded tread which further comprises means of illuminating a site to be photographed of the cut section at a predetermined angle in order to more clearly photograph differences in the gloss of the cut section.

The above and other objects, features and advantages of the present invention will become apparent from the following description taken into connection with the following drawings.

DETAILED DESCRIPTION OF THE PREFERRED EMBODIMENTS

A preferred embodiment of the present invention will be described hereinunder with reference to the accompanying drawings.

Figure 1:
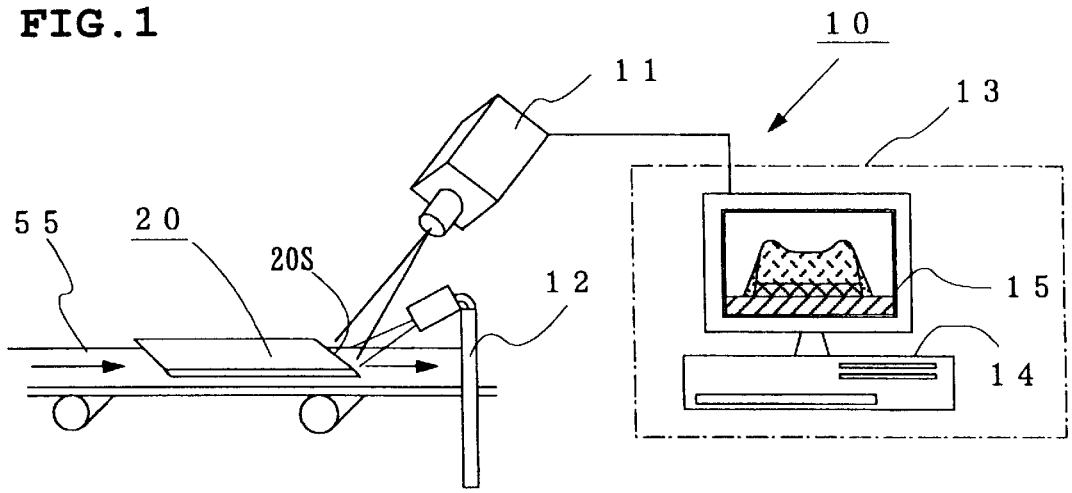
FIG. 1 is a diagram showing the outline of an apparatus for inspecting an extruded tread according to an Embodiment of the present invention.

FIG. 1 is a diagram showing the outline of an extruded tread inspection apparatus 10 according to an embodiment of the present invention. Reference numeral 11 denotes a CCD camera as photographing means installed obliquely above a belt conveyor 55 for conveying an extruded tread 20 after cutting, 12 an illuminator, located near the above belt conveyor 55, for illuminating the cut section 20S of the extruded tread 20 to be photographed at a predetermined angle, and 13 a tread internal structure inspection unit for inspecting the internal structure of the above extruded tread 20 by processing an image of the above cut section 20S for evaluation. In this embodiment, the tread internal structure inspection unit 13 is composed of a personal computer comprising a computer unit 14 for carrying out arithmetic processing such as image processing and the identification of the boundary and a display 15.

Figure 4:
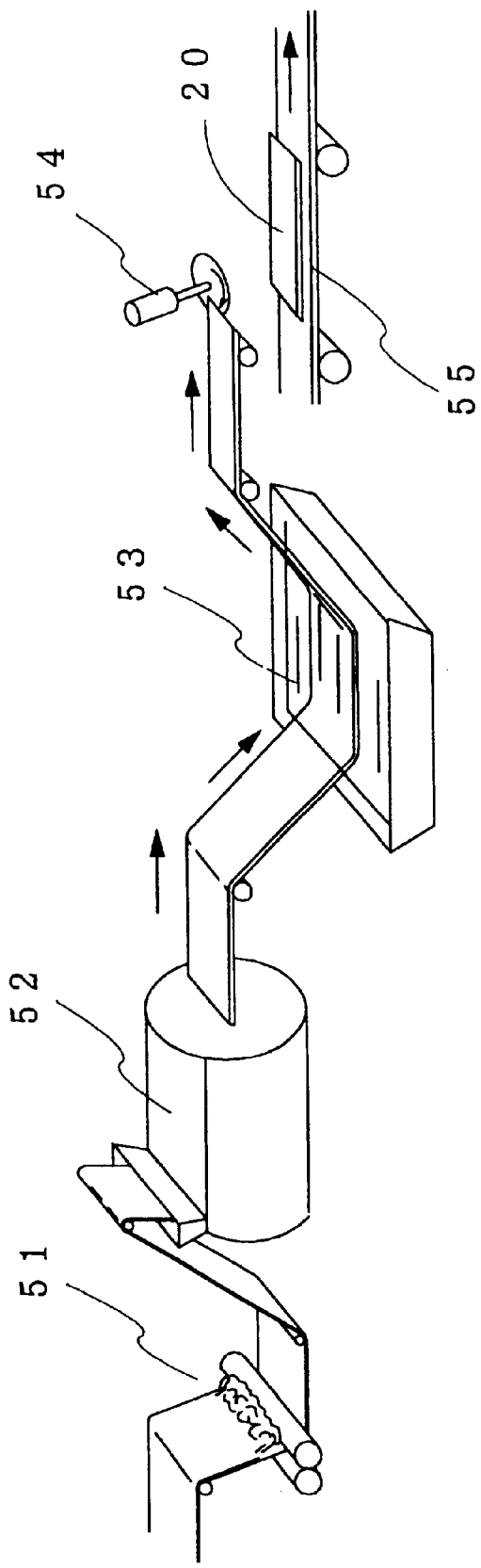
FIG. 4 is a diagram showing the outline of a tread extruding step.

It is conceivable that the installation site of the CCD camera 11 for photographing the section of the extruded tread molded to have a predetermined sectional form is near the cutting machine 54 shown in FIG. 4. However, in consideration of screening work after inspection, it is preferred to install the CCD camera at the conveyance line as in this embodiment.

Figure 2:
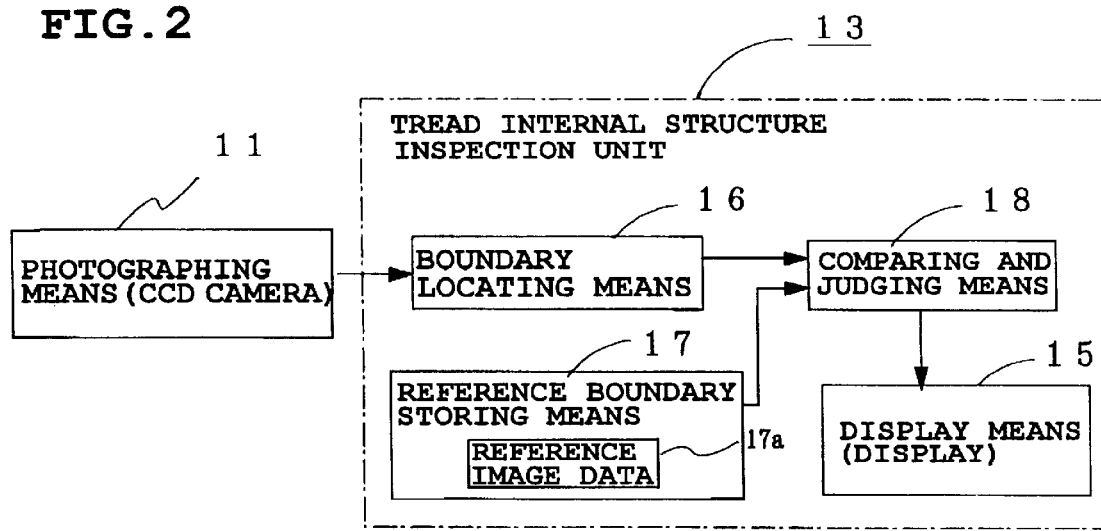
FIG. 2 is a functional block diagram of an apparatus for checking the internal structure of a tread according to the Embodiment of the present invention.

As shown in the functional block diagram of FIG. 2, the tread internal structure inspection unit 13 comprises boundary locating means 16 for processing image data on the cut section 20S of the extruded tread 20 photographed by the CD camera 11 to calculate the brightnesses of the rubber layers which differ in composition and locating the boundaries among the rubber layers on the above cut section 20S from differences among the calculated brightnesses of images of the rubber layers, and comparing and judging means 18 for comparing the boundaries of reference image data 17a on the sectional form of the tread recorded in reference boundary storing means 17 with the boundaries of image data on the sectional form of the tread which is processed by the above boundary locating means 16 to judge whether the internal structure of the photographed extruded tread 20 is satisfactory or not. Thus, the unit 13 processes an image of the cut section 20S photographed to judge whether the internal structure of the extruded tread 20 is satisfactory or not, and the image of the sectional form of the tread, the reference image and the result of the above decision are displayed on the display 15.

A description is subsequently given of the method of checking the internal structure of the extruded tread 20.

Figure 3A:
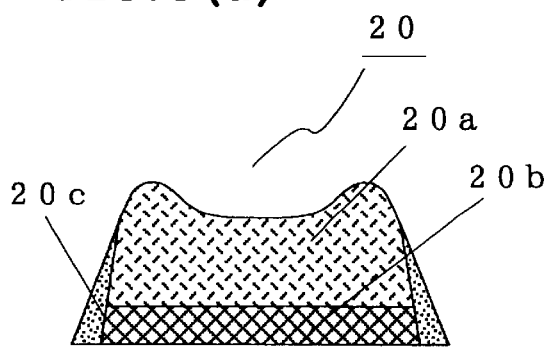
FIG. 3 is a diagram showing the cross section of an extruded tread.
Figure 3B:
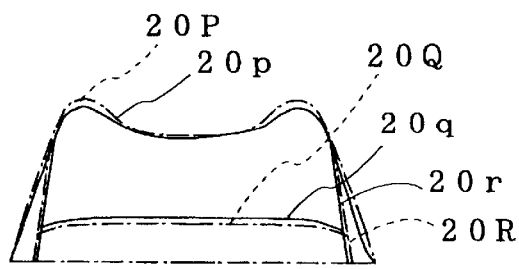

First, the cut section 20S of the cut extruded tread 20 conveyed by the belt conveyor 55 is photographed by the CCD camera 11 while being illuminated with the illuminator 12. This image data is then sent to the boundary locating means 16 of the tread internal structure inspection unit 13 to be processed. FIG. 3(*a*) is a diagram showing an example of the cut section 20S of the extruded tread 20. The above extruded tread 20 consists of three different rubber layers: a cap tread portion 20a on the road side, a base tread portion 20b on the inner side and a side portion 20c for laminating a side tread. These three rubber layers differ from one another in composition and there are gloss differences among the three rubber layers. Therefore, image data on the above cut section 20S is processed to calculate the brightnesses of the rubber layers which differ in composition and the boundaries among the above rubber layers 20a, 20b and 20c are located from differences in brightness so that the internal structure of the extruded tread 20 can be measured and displayed on the screen of the display 15.

In this embodiment, the reference image data 17a on the sectional form of the tread including the reference boundaries as the criteria of the above boundaries is stored in the reference boundary storing means 18 in advance and compared with the processed image data on the section of the tread by the comparing and judging means 18 so that it can be judged whether the internal structure of the photographed extruded tread 20 is satisfactory or not. That is, as shown in FIG. 3(*b*), the comparing and judging means 18 computes the amounts of dislocations of the boundaries 20p, 20q, 20r of the tread from the reference boundaries 20P, 20Q and 20R, respectively, and checks whether the above amounts of dislocations fall within the respective tolerances to judge whether the internal structure of the extruded tread 20 is satisfactory or not. The result of this decision is sent to unshown screening means and the unsatisfactory extruded tread is eliminated from the production line.

Thus, the internal structure of the extruded tread 20 is judged by image processing, thereby making it possible to easily and accurately judge whether the tread is good or bad and enabling the on-line measurement of the tread. Therefore, the temporary reservation of extruded products can be avoided. As a result, the number of measurement steps can be reduced, the efficiencies of the steps can be increased and also inspection can be shifted to the inspection of all the treads from sampling inspection. Therefore, all tread quality guarantee system can be established to ensure a higher level of quality for each tread.

In the above embodiment, the extruded tread 20 consists of three layers. The present invention is not limited to this. If it is a laminate consisting of rubber layers which differ in composition, it is needless to say that the boundaries among the rubber layers can be located in the same manner as the above-described embodiment.

In the above embodiment, the comparing and judging means 18 judges whether the internal structure of the extruded tread 20 is satisfactory or not by arithmetic operations. The operator may judge whether the internal structure is satisfactory or not from an image shown in the above FIG. 3(*b*) and displayed on the screen of the display 15. Since the reference boundaries 20P, 20Q and 20R are displayed on the image, it is easy to judge whether the internal structure is satisfactory or not. When the tolerances of the boundaries among rubber layers are displayed on the image at the same time, even an unskilled operator can judge whether the internal structure is satisfactory or not easily from the above image.

In the above embodiment, the boundaries among the rubber layers 20a, 20b and 20c which differ in composition are located. The lamination state of the rubber layers 20a, 20b and 20c can also be checked by comparing the thicknesses of the boundaries.

Further, the present invention is not limited to checking of the internal structure of the extruded tread 20 and can be applied to the measurement and inspection of the internal structure and the lamination accuracy of a composite member.

As having been described above, according to the present invention, the cut section of the extruded tread is photographed, the obtained image is processed, and the boundaries among the rubber layers which differ in composition on the cut section are located from differences in brightness among the rubber layers of the image. Therefore, the boundaries among the rubber layers can be identified easily and accurately and the internal structure of the extruded tread can be inspected without extracting an inspection sample from the production lot, thereby making it possible to shift to the inspection of all the treads and further improve the quality of each tread.

What is claimed is:

1. A method of inspecting an extruded tread, comprising the steps of:

photographing the cut section of an extruded tread;

processing the obtained image; and locating the boundaries among rubber layers on the above cut section from differences in brightness among the rubber layers which differ in composition.

2. An apparatus for inspecting an extruded tread, comprising:

means for photographing the cut section of an extruded tread, the means being installed near a line for conveying the extruded tread after cutting;

means for processing an image of the photographed cut section of the extruded tread to locate the boundaries among rubber layers which differ in composition on the cut section from differences in brightness among the rubber layers of the image; and means for checking whether the internal structure of the extruded tread is satisfactory or not by comparing the above located boundaries with preset reference boundaries.

3. The apparatus for inspecting an extruded tread according to claim 2 which further comprises means for illuminating a site to be photographed of the cut section at a predetermined angle.

* * * * *